United States Patent [19]

Porter et al.

[11] Patent Number: 4,589,288
[45] Date of Patent: May 20, 1986

[54] STATIC BENDING APPARATUS FOR GRADING WOOD PANELS

[75] Inventors: Andrew W. Porter, Richmond; Lars Bach, Edmonton, both of Canada

[73] Assignee: Her Majesty the Queen in right of the Province of Alberta, as represented by the Minister of Energy and Natural Resources, Edmonton, Canada

[21] Appl. No.: 700,111

[22] Filed: Feb. 8, 1985

[51] Int. Cl.$^4$ .............................................. G01N 3/20
[52] U.S. Cl. ......................................... 73/852; 73/849
[58] Field of Search .................. 73/852, 849, 812, 785

[56] References Cited

U.S. PATENT DOCUMENTS

| | | | |
|---|---|---|---|
| 3,194,063 | 7/1965 | McKean | 73/852 |
| 4,213,349 | 7/1980 | Miura | 73/852 |
| 4,313,348 | 2/1982 | Madsen | 73/852 |

Primary Examiner—Anthony V. Ciarlante

[57] ABSTRACT

A non-destructive method and apparatus is provided for testing a wood panel, such as a sheet of plywood, to establish values which may be used in calculating a measure of the modulus of elasticity (MOE) for the panel. The invention involves supporting the bottom surface of the panel horizontally with two spaced parallel rollers and contacting the top surface of the panel with a pivotally mounted loading bar which is adapted to apply linear loading to the panel substantially uniformly across its width, even though the panel may be warped or bent. The loading bar is biased by a double-acting cylinder so as to apply a first load and then, in quick succession, a second incremental load. The two loads are selected so as to fall on the substantially linear portion of the load deflection curve for the panel. The magnitudes of the two loads are measured with suitable means, such as a load cell. The extension or distance moved by the cylinder in applying the incremental load is known or measured. With the two loadings and the incremental deflection established, one can calculate, using standard formulae, a value which is found to closely approximate the MOE.

6 Claims, 6 Drawing Figures

Fig. 3.

STATIC BENDING APPARATUS FOR GRADING WOOD PANELS

FIELD OF THE INVENTION

The invention relates to a method and apparatus for the nondestructive testing of a reconstituted wood panel, such as a sheet of plywood.

BACKGROUND OF THE INVENTION

Wood panels, generically termed "reconstituted wood panels", include such fabricated products as plywood, flakeboard, hardboard, particleboard, waferboard, oriented strand board and the like. Such panels are manufactured in the form of large relatively thin sheets. Typically, such a panel might be about four feet in width and eight feet in length.

As a consequence of the process of manufacture, such panels display a greater propensity to warpage and sagging than a natural wood product.

It is desirable to be able to establish, at a relatively high speed and in a non-destructive fashion, values for the panel which can be used to calculate a measure of the stiffness of the panel. We have found that the stiffness of a panel correlates with the modulus of elasticity (MOE), and, as a result, with the modulus of rupture (MOR) of the panel.

At this time, to our knowledge, there is no machine available which can, in a matter of seconds, grade a panel by yielding such values. There is, in common use in the industry, a machine known as the Post Flexure machine. In the use of this machine, the panel is threaded on edge into two spaced vertical frames, which frames are then rotated in opposite directions to flex the central part of the panel. The values for the force used to effect rotation, and the extent of deflection effected are used in suitable equations to calculate a value representative of MOE. However, this machine is not suitable for grading on a production line, as it takes several minutes to test a panel with it.

We evolved the following criteria for a machine that could be used to grade wood panels:

(1) it must accommodate the large panels;

(2) it must distribute the deflecting load substantially uniformly and linearly across the full width of the panel, in spite of the warped or sagging nature of said panel;

(3) it must cope with the fact that the load deflection (or moment vs. deflection) curve for a wood panel is not, typically, linear in the proximity of the zero point; and (4) it must be relatively fast in operation and capable of being upgraded to production line speeds.

SUMMARY OF THE INVENTION

The invention involves applying a first linear load to one major surface of the panel while supporting it on the opposite side with two spaced apart linear supports which bracket the loading member. The load is applied with a loading member which can pivot in a plane perpendicular to the main surface of the panel, to permit the loading member to conform to the warped or sagging surface of the panel. The load which is applied is selected so as to fall on the substantially linear portion of the load deflection curve for the panel. Once the panel has been deflected in this manner, the loading is then incrementally increased, causing further deflection. The two loadings and the incremental deflection distance are noted or measured. These three measurements can then be used to compute a reasonably accurate estimate of the MOE and MOR.

Broadly stated, the invention in one aspect comprises an apparatus, for non-destructive testing of a reconstituted wood panel, characterized by having a substantially linear relationship between load and deflection when tested to develop a load deflection curve, comprising: a support frame; means, associated with the support frame, for bearing against one major surface of the panel along two spaced apart parallel lines extending substantially across the width of the panel; means, associated with the support frame, for bearing against the other major surface of the panel along a line extending substantially across the width of the panel between the aforesaid spaced lines of contact; one of said bearing means being pivotally mounted on said support frame for pivoting in a plane generally perpendicular to the main plane of the panel, whereby it may conform closely with the panel surface to apply a substantially linear and uniform load across substantially the width of the panel; means for biasing the load-applying bearing means to apply a first load to the panel, said first load being selected to fall on the substantially linear portion of the load deflection curve for the panel, to thereby deflect the panel across its width a first distance; and means for further biasing the load-applying bearing means to apply an incremental load, also falling on said linear portion, to the panel to thereby further deflect the panel a second distance.

In another aspect, the invention comprises a method for testing the stiffness of a reconstituted wood panel, characterized by having a substantially linear relationship between load and deflection when tested to develop a load deflection curve, comprising: contacting one major surface of the panel substantially across its width with a loading member and biasing said member to apply a substantially linear and uniform first load to the panel while supporting the other major surface of the panel along two spaced lines bracketing and parallel to the line of application of said first load, to thereby deflect the panel, said load being of a magnitude to fall on the substantially linear portion of the load deflection curve for the panel; determining the magnitude of the first load to obtain a first measurement; further biasing the loading member in quick succession to apply an incremental load, also falling on said linear portion, to the panel and further deflect said panel through a predetermined distance; and determining the magnitude of the first load and the extent of the deflection to obtain second and third measurements; and using the measurements obtained to compute a measure of the stiffness of the panel.

DESCRIPTION OF THE DRAWINGS

FIG. 2 is a 3-part sectional schematic view of the loading bar, double-acting cylinder, load cell, and universal pivot, which together make up the deflecting assembly, with the cylinder shown in the beginning mode (FIG. 2a), first loading mode (FIG. 2b), and second loading mode (FIG. 2c);

DESCRIPTION OF THE PREFERRED EMBODIMENT

In General

Figure 1:
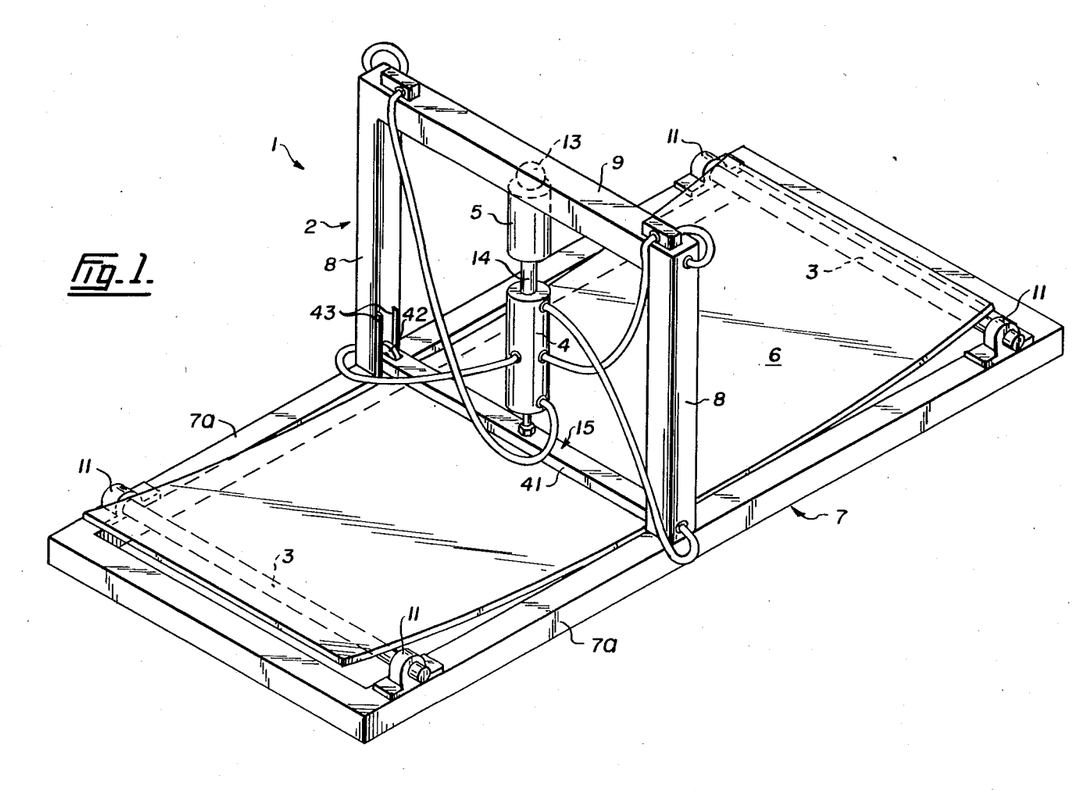
FIG. 1 is a perspective view of the apparatus, showing a panel undergoing deflection.

The static bending apparatus 1 comprises, in general, a frame 2, a pair of support rollers 3, a pivoted load-applying two-stage cylinder assembly 4, and a load cell 5. The rollers 3 support the wood panel 6 to be tested. The cylinder assembly 4 applies two different and sequential loadings, to pre-load and then incrementally load the panel to deflect the latter through a pre-determined distance. The load cell 5 provides a measure of the loading applied. And the frame 2 carries the aforementioned components.

The Support Frame

The support frame 2 comprises a horizontal, rectangular section 7. A pair of vertically extending posts 8 project upwardly from the side members 7a of the section 7, substantially at their mid-points. A horizontal beam 9 extends between the posts 8 and is supported thereby. The beam 9 is therefore positioned to extend transversely across the rectangular section 7, substantially at its mid-point, and in vertically spaced relation thereabove. The rectangular section 7 is of sufficient width and length so as to accommodate the wood panel 6.

The Supports

A pair of parallel, spaced apart, elongate support rollers 3 are each supported by a pair of pillow blocks 11, which pillow blocks are mounted on the rectangular section side members 7a adjacent the latters' ends. The wood panel 6 may thus be supported by the rollers 3 from below and across its width, at points adjacent each of its ends.

There is thus provided means, associated with the support frame, for bearing against one major surface of the panel along two spaced, parallel lines extending substantially across the width of the panel.

The rollers 3 are utilized to provide the desired two spaced end supports for the panel, while offering no frictional resistance to panel movement which arises from central deflection thereof.

The Load Cell and Cylinder Assembly

Figure 2A:
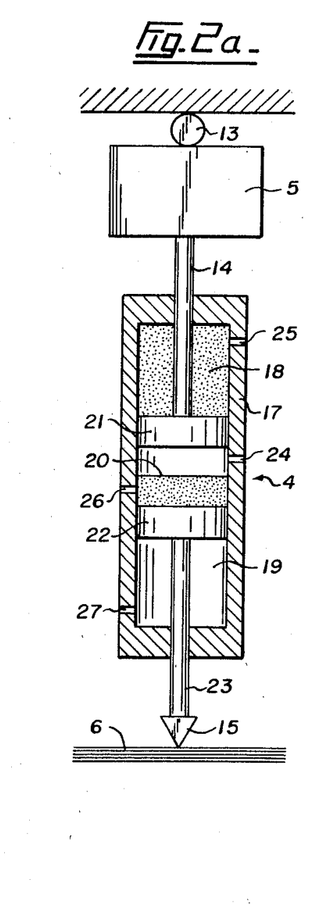
Figure 2B:
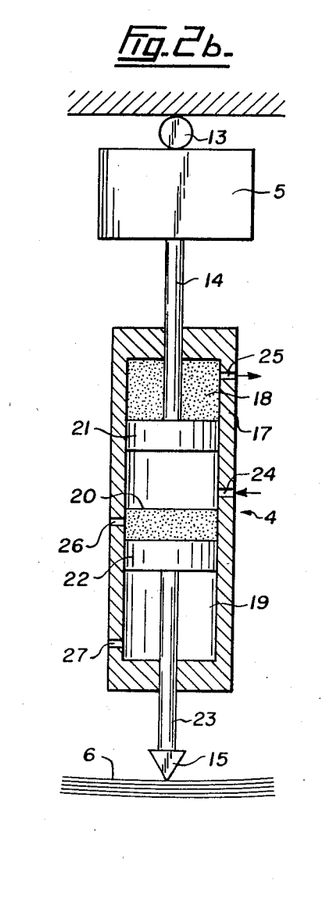
Figure 2C:
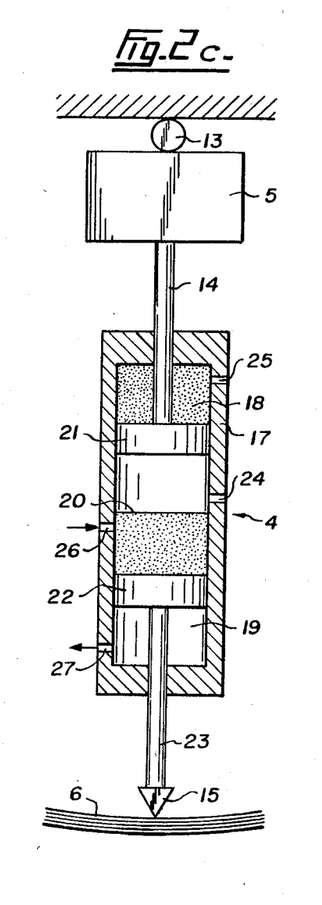

The load cell 5 is mounted to the underside of the beam 9 by a universal joint 13. The load cell 5 is connected to the piston rod 14 of the two-stage cylinder assembly 4. At its lower end, the cylinder assembly 4 includes an attached loading bar 15, which may be biased to press against the wood panel 6, to deflect the latter.

The cylinder assembly 4 comprises a cylinder body 17 which forms upper and lower chambers 18, 19 separated by a divider 20. A piston 21 is disposed in upper chamber 18 and, as previously mentioned, its piston rod 14 is connected to the load cell 5. A second piston 22 is disposed in the lower chamber 19 and its piston rod 23 is connected to the loading bar 15.

A port 24, for admitting and exhausting of pressurized air, communicates through the cylinder body wall with the bottom end of the upper chamber 18. A port 25, for admitting and exhausting of oil, communicates with the top end of the upper chamber 18.

Turning now to the lower chamber 19, a port, 26 for admitting and exhausting of oil, communicates with the top end of said lower chamber. And a port 27, for admitting and exhausting of pressurized air, communicates with the lower end of the lower chamber 19.

Figure 3:
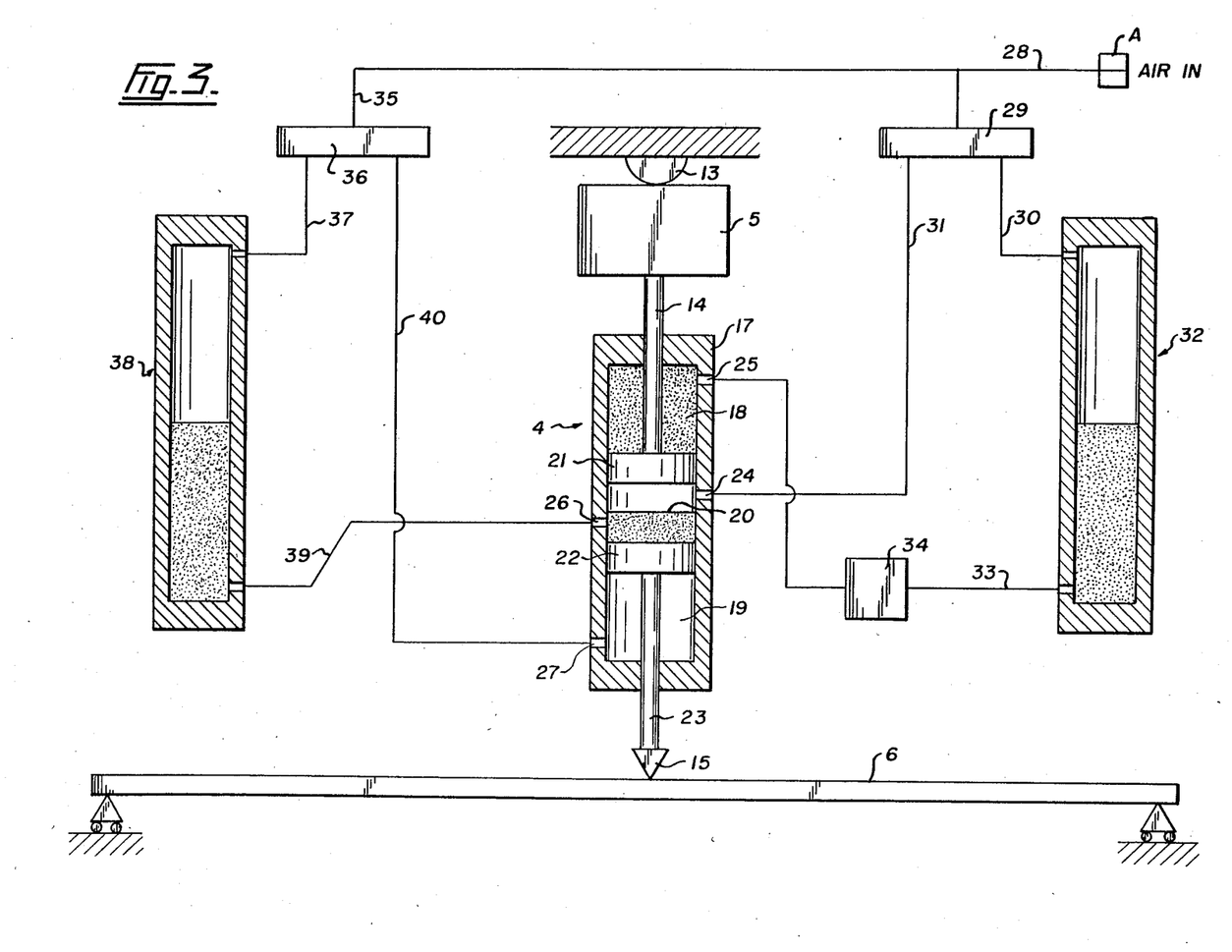
FIG. 3 is a schematic view showing the pneumatic-hydraulic actuating circuit, the deflecting assembly, the panel, and the support means.

Having reference to the pneumatic-hydraulic circuit shown in FIG. 3, a source A of pressurized air supplies air through line 28 to a 4-way pneumatic valve 29.

The air can move from this valve 29 through either line 30 or 31. Line 30 connects with the upper end of the pre-load oil reservoir cylinder 32. This pre-load reservoir cylinder 32 connects at its base with a line 33. The line 33 is controlled by a 2-way normally closed valve 34 and connects with the port 25 at the top end of the upper chamber 18. Line 31 connects with the port 24 at the lower end of the upper chamber 18.

The air source A is also connected through line 35 with 4-way pneumatic valve 36. A line 37 connects the valve 36 with the upper end of the final load reservoir cylinder 38. The lower end of cylinder 38 is connected by line 39 with the port 26 leading into the upper end of the lower chamber 19. The valve 36 is also connected by a line 40 with the port 27 leading into the lower end of the lower chamber 19.

By means of this arrangement, one can first open the valve 29 and admit pressurized air from source A through lines 28 and 30 into the pre-load reservoir cylinder 32. Upon opening the valve 34, oil is forced by the air from cylinder 32 through line 33 and valve 34, to fill the upper end of the upper chamber 18. Valve 34 is then closed and the oil in chamber 18 is 'locked' in place. Valve 36 can also be opened to admit air through line 37 into the final load reservoir cylinder 38 and force oil through line 39 to the upper end of lower chamber 19. Valve 36 can then be switched to introduce air through line 40 to the lower end of chamber 19. At this point, the system is ready for use. Both pistons 22 and 21 are adjacent the divider 20 and piston rod 23 is fully retracted.

Figure 4:
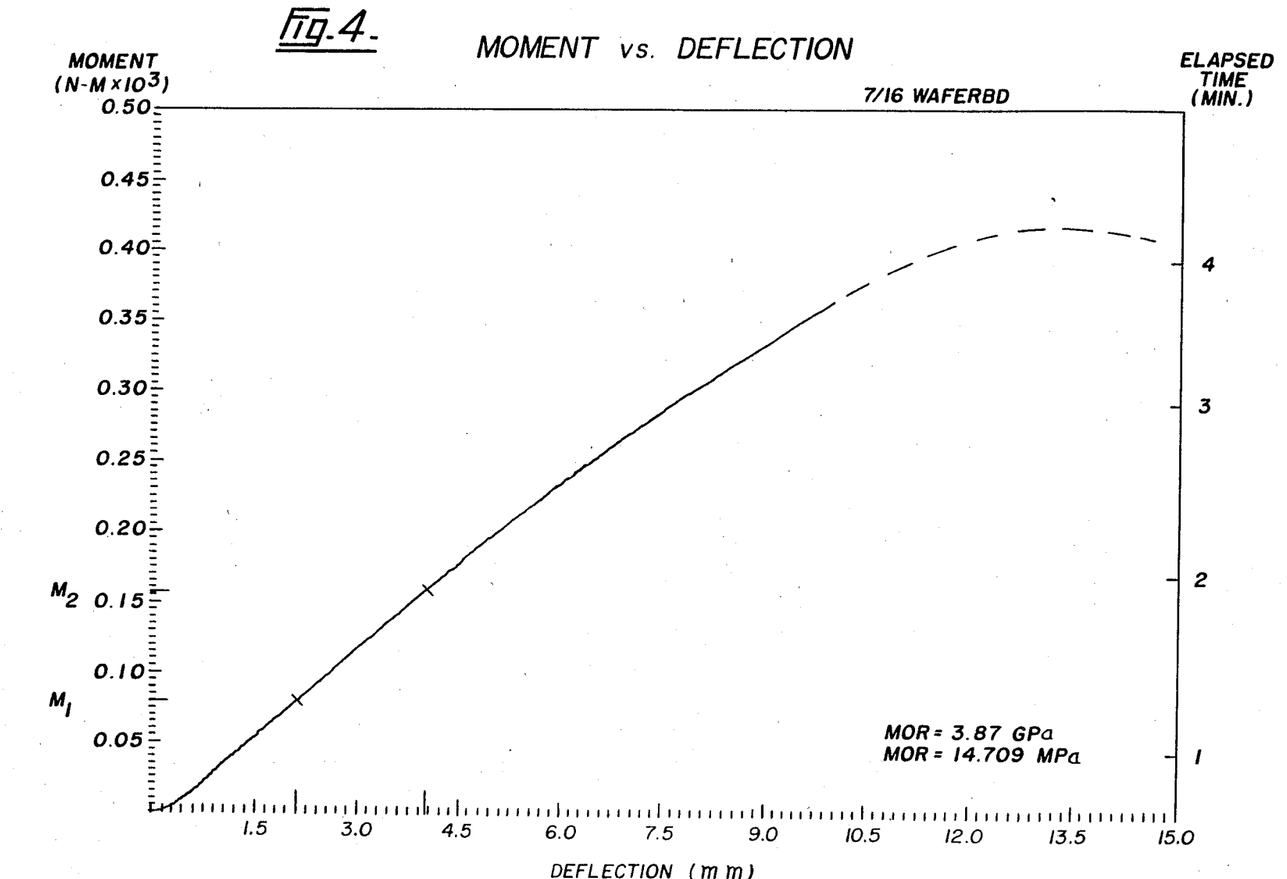
FIG. 4 is a typical load deflection curve for a wood panel, developed using a Post flexure machine—the non-linear and linear portions of the curve are identified.

To initiate testing of a panel, the valve 29 is opened to admit air through line 31 and port 24 into the lower end of upper chamber 18. At the same time, valve 34 is opened to allow oil to be exhausted from chamber 18 into reservoir cylinder 32. As a result, the cylinder body 17 is forced downward and the piston rod 23 and loading bar 15 press downwardly against the panel. The force being applied by the loading bar 15 is monitored on the load cell 5, until it reaches a pre-determined value. This value is selected to correspond with a point that is safely on the linear portion of the moment vs deflection curve for a panel of the type being tested. A typical example of such a curve is shown in FIG. 4. At this stage, valve 34 is closed, so that the pre-load force being applied to the panel is maintained.

The valve 36 is then opened to apply air pressure through line 37 to force oil from cylinder 38 into the upper end of the lower chamber 19. This causes the piston 22 and rod 23 to move downwardly through a known travel, being the full stroke of the piston 22. When this stroke is complete, the force being exerted by the loading bar 15 is noted from the load cell 5.

The circuit is then returned to the starting condition by opening line 37 through valve 36, admitting air through valve 36 and line 40 to retract the piston 22, and opening valve 34 and admitting air through valve 29 and line 30 to depress piston 21.

By virtue of this arrangement, the following steps occur:

(1) the panel is deflected to a limited extent by applying a load of pre-determined magnitude;

(2) the panel is then further deflected through a known distance and the magnitude of the incremental load required to achieve this is measured.

From the values for the pre-load, the incremental load, the deflecting arising from the incremental load and the known span and width of the panel, the stiffness of the panel can be calculated. A close approximation of the MOE can be calculated if the thickness of the panel is known.

Loading bar 15 contacts the mid-point of panel 6 from above, transmitting the loads supplied by cylinder assembly 4 to said panel. Loading bar 15 consists of an elongate rod 41 having a sheaved wheel 42 at each end thereof. The bar 15 is operative to distribute the applied loads substantially uniformly across the panel width as a line load. The loading bar 15 is threadably engaged to the lower end of lower piston rod 23 and is operative to move concomitantly therewith. Sheaved wheels 42 engage guides 43 mounted on posts 8 and function to maintain the bar 15 in longitudinal alignment. Provision of universal joint 13 ensures good contact between bar 15 and panel 6, irrespective of warping, sagging, or surface irregularities thereof.

Stated otherwise, there is provided means for bearing against the upper major surface of the panel along a line extending substantially across the width of the panel, which means are pivotally mounted on the support frame for pivoting in a plane generally perpendicular to the main plane of the panel, whereby said bearing means may conform closely with the panel surface to apply a substantially linear and uniform load across substantially the width of the panel.

EXAMPLE

This example shows the close correlation, in the calculated MOE results, which is obtained by the use of the present apparatus and the industry-accepted Post flexure apparatus.

Testing was conducted following the requirements of ASTM D 3043-76 (1981) Method C for the Post flexure apparatus.

The present apparatus was operated in accordance with the following specific conditions:

The support rollers for plywood sample M-1-A were chosen to be spaced 1118 mm and the initial pre-determined stress level for preload was 3.5 MPa. This sample was 1219 mm wide and had a thickness of 9.44 mm. The incremental deflection following preloading was chosen to be 12.75 mm.

The materials tested were nominally 1220×2440×9.5 mm panels of softwood plywood and 1220×2440×11.1 mm panels of waferboard.

The test procedure followed with respect to using both machines was as follows:

1. Each 1220×2440 mm sheet was cut into two 1220×1220 mm samples. Half were designated as A—for testing parallel to the grain direction (or along the length in the case of undirectional boards) and half were designated B—for testing across the grain direction (or along the width);
2. Parallel and cross dimensions were measured at mid-span;
3. Thickness was measured at the middle of each edge and the average of the four values recorded;
4. All of the A panels, then all of the B panels were tested on the present (MSR) machine;
5. A check was made to ensure that the two load levels from the MSR machine testing (preload and final load) both fell on the straight line portion of the load deflection plot from the Post flexure machine testing, shown in FIG. 4; and
6. All of the A panels and then all of the B panels were tested to failure on the Post flexure machine (per ASTM D 3043C-76).

The data derived from testing the MSR machine was used to compute MOE using the following equation:

$$MOE = \frac{L^3}{4 \cdot b \cdot d^3} \cdot \frac{\Delta p}{\Delta y}$$

where:
b = width of specimen in millimeters
d = average thickness of specimen in millimeters
L = length of span in millimeters
$\Delta p/\Delta y$ = slope of the load deflection curve derived using two points established by the pre-load and incremental load.

The MOE from the Post flexure testing was calculated using the computations required by the aforesaid ASTM standard.

The results from the testing were as follows:

TABLE A

SUMMARY OF TESTING - MSR* AND POST FLEXURE

| Sample Number | Thick. mm | MSR MOE MPa | Post Flexure MOE MPa |
|---|---|---|---|
| M-1-A | 9.44 | 8,580 | 8,810 |
| M-2-A | 9.31 | 8,910 | 9,130 |
| M-3-A | 9.38 | 8,870 | 9,620 |
| M-4-A | 9.20 | 10,190 | 10,780 |
| M-5-A | 9.16 | 9,210 | 9,860 |
| M-6-A | 9.34 | 8,530 | 8,540 |
| M-7-A | 9.14 | 8,990 | 10,000 |
| M-8-A | 9.81 | 8,650 | 8,610 |
| M-9-A | 9.18 | 10,350 | 10,700 |
| M-10-A | 9.29 | 9,390 | 9,250 |
| M-11-A | 9.52 | 8,690 | 9,060 |
| M-12-A | 9.31 | 9,410 | 9,380 |
| M-13-A | 9.31 | 8,890 | 8,840 |
| M-14-A | 8.87 | 11,570 | 11,410 |
| M-15-A | 9.38 | 10,320 | 10,750 |
| M-16-A | 9.14 | 10,850 | 11,360 |
| M-17-A | 9.16 | 10,210 | 10,070 |
| M-18-A | 9.23 | 9,670 | 9,630 |
| M-19-A | 9.16 | 10,720 | 10,530 |
| M-20-A | 9.13 | 10,380 | 10,400 |
| Average | 9.27 | 9,620 | 9,840 |

Test Material - 9.5 mm Spruce Plywood
Test Direction - Machine or Parallel Direction
Conditioning - As Received
Predetermined Initial Stress Level - 3.5 MPa
Stroke of Final Load Cylinder - 12.75 mm
Test Span - 1118 mm

| Sample Number | Thick. mm | MSR MOE MPa | Post Flexure MOE MPa |
|---|---|---|---|
| T-1-B | 9.54 | 700 | 740 |
| T-2-B | 9.39 | 540 | 520 |
| T-3-B | 9.50 | 790 | 800 |
| T-4-B | 9.26 | 590 | 640 |
| T-5-B | 9.18 | 580 | 620 |
| T-6-B | 9.54 | 610 | 580 |
| T-7-B | 9.40 | 780 | 720 |
| T-8-B | 9.84 | 540 | 560 |
| T-9-B | 9.12 | 700 | 710 |
| T-10-B | 9.28 | 620 | 670 |
| T-11-B | 9.59 | 710 | 760 |
| T-12-B | 9.30 | 660 | 730 |
| T-13-B | 9.42 | 920 | 1,060 |
| T-14-B | 9.07 | 560 | 700 |
| T-15-B | 9.41 | 620 | 740 |
| T-16-B | 9.33 | 580 | — |
| T-17-B | 9.09 | 660 | 850 |
| T-18-B | 9.02 | 550 | — |
| T-19-B | 9.14 | 650 | 790 |
| T-20-B | 8.98 | 580 | 760 |
| Average | 9.32 | 650 | 720 |

TABLE A-continued
SUMMARY OF TESTING - MSR* AND POST FLEXURE

| Sample Number | Thick. mm | MSR MOE MPa | Post Flexure MOE MPa |
|---|---|---|---|
| Test Material - 9.5 mm Spruce Plywood | | | |
| Test Direction - Transverse Direction | | | |
| Conditioning - As Received | | | |
| Predetermining Initial Stress Level - 0.8 MPa | | | |
| Stroke of Final Load Cylinder - 12.75 mm | | | |
| Test Span - 1118 mm | | | |
| U1A | 11.09 | 4,360 | 4,260 |
| U2A | 11.20 | 4,460 | 4,630 |
| U3A | 11.28 | 4,280 | 4,430 |
| U4A | 10.44 | 3,920 | 3,890 |
| U5A | 12.17 | 3,860 | 4,040 |
| U6A | 11.45 | 4,320 | 4,370 |
| U7A | 10.86 | 4,040 | 4,020 |
| U8A | 11.76 | 4,420 | 4,530 |
| U9A | 11.99 | 4,380 | 4,520 |
| U10A | 11.57 | 4,710 | 5,020 |
| U11A | 11.71 | 4,470 | 4,690 |
| U12A | 11.30 | 4,760 | 5,140 |
| U13A | 11.90 | 4,310 | 4,560 |
| U14A | 11.19 | 4,930 | 5,390 |
| U15A | 11.83 | 4,320 | 4,480 |
| U16A | 11.47 | 4,570 | 4,700 |
| U17A | 11.22 | 4,850 | 4,890 |
| U18A | 12.09 | 3,880 | 3,820 |
| U19A | 11.21 | 5,150 | 5,310 |
| U20A | 12.00 | 4,210 | 4,170 |
| Average | 11.49 | 4,410 | 4,540 |
| Test Run - Waferboard | | | |
| Nominal Thickness - 11.1 mm | | | |
| Test Direction - Parallel to Machine Direction | | | |
| Predetermined Initial Stress Level - 2.758 MPa | | | |
| Stroke of Final Cylinder - 12.75 mm | | | |
| Test Span - 1118 mm | | | |
| U1B | 11.13 | 3,920 | 3,980 |
| U2B | 10.82 | 3,750 | 3,930 |
| U3B | 11.34 | 4,300 | 4,470 |
| U4B | 10.74 | 4,070 | 4,360 |
| U5B | 11.50 | 4,020 | 4,390 |
| U6B | 11.81 | 3,700 | 3,870 |
| U7B | 10.90 | 4,360 | 4,430 |
| U8B | 12.02 | 3,680 | 3,900 |
| U9B | 11.49 | 4,150 | 4,500 |
| U10B | 11.62 | 3,900 | 4,160 |
| U11B | 11.61 | 3,900 | 4,090 |
| U12B | 11.56 | 3,780 | 3,830 |
| U13B | 11.67 | 4,380 | 4,700 |
| U14B | 11.36 | 4,610 | 4,820 |
| U15B | 11.68 | 4,270 | 4,650 |
| U16B | 11.90 | 3,940 | 4,240 |
| U17B | 11.69 | 4,300 | 4,570 |
| U18B | 11.26 | 4,680 | 4,950 |
| U19B | 11.43 | 4,480 | 4,640 |
| U20B | 11.27 | 4,660 | 5,020 |
| Average | 11.44 | 4,140 | 4,380 |
| Test Run - Waferboard | | | |
| Nominal Thickness - 11.1 mm | | | |
| Test Direction - Waferboard Across Machine Direction | | | |
| Predetermined Initial Initial Stress Level - 2.758 MPa | | | |
| Stroke of Final Cylinder - 12.75 mm | | | |
| Test Span - 1118 mm | | | |

*MSR designates the present machine

The embodiments of the invention in which an exclusive property or privilege is claimed are defined as follows:

1. An apparatus for non-destructive testing of a reconstituted wood panel, characterized by having a substantially linear relationship between load and deflection when tested to develop a load deflection curve, comprising:
   a support frame;
   means, associated with the support frame, for bearing against one major surface of the panel along two spaced parallel lines extending substantially across the width of the panel;
   means, associated with the support frame, for bearing against the other major surface of the panel along a line extending substantially across the width of the panel between the aforesaid spaced lines of contact;
   one of said bearing means being pivotally mounted on said support frame for pivoting in a plane generally perpendicular to the main plane of the panel, whereby it may conform closely with the panel surface to apply a substantially linear and uniform load across substantially the width of the panel;
   means for biasing the load-applying bearing means to apply a first load to the panel, said first load being selected to fall on the substantially linear portion of the load deflection curve for the panel, to thereby deflect the panel across its width a first distance; and
   means for further biasing the load-applying bearing means to apply an incremental load, also falling on said linear portion, to the panel to thereby further deflect the panel a second distance.

2. An apparatus for non-destructive testing of a reconstituted wood panel, characterized by having a substantially linear relationship between load and deflection when tested to develop a load deflection curve, comprising:
   a support frame;
   first means, associated with the support frame, for bearing against the bottom surface of the panel along two spaced parallel lines extending substantially across the width of the panel;
   second means, associated with the support frame, for bearing against the top surface of the panel along a line extending substantially across the width of the panel between the aforesaid spaced lines of contact;
   said second means being pivotally mounted on said support frame for pivoting in a plane generally perpendicular to the main plane of the panel, whereby it may conform closely with the panel surface to apply a substantially linear and uniform load across substanially the width of the panel;
   third means, associated with the support frame, for biasing the second means to apply a first load to the panel, said first load being of a magnitude to fall on the substantially linear portion of the load deflection curve for the panel, to thereby deflect the panel across its width a first distance; and
   fourth means, associated with the support frame, for further biasing the second means to apply an incremental load, also falling on said linear portion, to the panel to thereby further deflect the panel a second distance.

3. The apparatus as set forth in claim 2 wherein:
   the first means comprises a pair of horizontally aligned rotatable members mounted on the support frame.

4. The apparatus as set forth in claim 2 wherein:
   the third and fourth means comprises a double-acting cylinder connected at one end with the support frame and at the other end with the second means, whereby extension of one end of the cylinder through a pre-determined travel applies said first load and extension of the other end of the cylinder through a pre-determined travel applies said incremental load and establishes the deflection undergone by the panel when the incremental load is applied.

5. The apparatus as set forth in claim 3 wherein:
the third and fourth means comprises a double-acting cylinder connected at one end with the support frame and at the other end with the second means, whereby extension of one end of the cylinder through a pre-determined travel applies said first load and extension of the other end of the cylinder through a pre-determined travel applies said incremental load and establishes the deflection undergone by the panel when the incremental load is applied.

6. A method for testing the stiffness of a reconstituted wood panel, characterized by having a substantially linear relationship between load and deflection when tested to develop a load deflection curve, comprising:
contacting one major surface of the panel substantially across its width with a loading member and biasing said member to apply a substantially linear and uniform first load to the panel while supporting the other major surface of the panel along two spaced lines bracketing and parallel to the line of application of said first load, to thereby deflect the panel, said load being of a magnitude to fall on the substantially linear portion of the load deflection curve for the panel;

determining the magnitude of the first load to obtain a first measurement;

further biasing the loading member in quick succession to apply an incremental load, also falling on said linear portion, to the panel and further deflect said panel through a pre-determined distance; and determining the magnitude of the first load and the extent of the deflection to obtain second and third measurements; and using the measurements obtained to compute a measure of the stiffness of the panel.

* * * * *

UNITED STATES PATENT AND TRADEMARK OFFICE
CERTIFICATE OF CORRECTION

PATENT NO. : 4,589,288
DATED : May 20, 1986
INVENTOR(S) : Andrew W. Porter, Lars Bach It is certified that error appears in the above—identified patent and that said Letters Patent is hereby corrected as shown below:

Column 10, line 13 - "first" should read "incremental"

Signed and Sealed this

Sixth Day of October, 1987

Attest:

DONALD J. QUIGG

*Attesting Officer*  *Commissioner of Patents and Trademarks*